United States Patent
Prieels (10) Patent No.: US 9,283,406 B2
(45) Date of Patent: Mar. 15, 2016

(54) CHARGED HADRON BEAM DELIVERY

(71) Applicant: IOM BEAM APPLICATIONS S.A., Louvain-la-Neuve (BE)

(72) Inventor: Damien Prieels, Court-Saint-Etienne (BE)

(73) Assignee: IOM BEAM APPLICATIONS S.A., Louvain-la-Neuve (BE)

( * ) Notice: Subject to any disclaimer, the term of this patent is extended or adjusted under 35 U.S.C. 154(b) by 46 days.

(21) Appl. No.: 14/493,440

(22) Filed: Sep. 23, 2014

(65) Prior Publication Data

US 2015/0094517 A1    Apr. 2, 2015

(30) Foreign Application Priority Data

Sep. 30, 2013    (EP) .................................... 13186787

(51) Int. Cl.
| | |
|---|---|
| *A61N 5/10* | (2006.01) |
| *G21K 5/10* | (2006.01) |
| *G21K 5/04* | (2006.01) |
| *G01R 33/48* | (2006.01) |

(52) U.S. Cl.
CPC ............ *A61N 5/1077* (2013.01); *A61N 5/1043* (2013.01); *A61N 5/1048* (2013.01); *G01R 33/4808* (2013.01); *G21K 5/04* (2013.01); *G21K 5/10* (2013.01); *A61N 5/107* (2013.01); *A61N 2005/1055* (2013.01); *A61N 2005/1087* (2013.01)

(58) Field of Classification Search
CPC . A61N 5/1043; A61N 5/1077; A61N 5/1048; A61N 2005/1087; A61N 2005/1055; G01R 33/481; G21K 5/04; G21K 5/10
See application file for complete search history.

(56) References Cited

U.S. PATENT DOCUMENTS

| | | | |
|---|---|---|---|
| 6,268,610 B1 * | 7/2001 | Pu ........................... | A61N 5/10 250/398 |
| 6,717,162 B1 * | 4/2004 | Jongen ................. | A61N 5/1042 250/492.1 |
| 6,881,970 B2 * | 4/2005 | Akiyama ................. | A61N 5/10 250/307 |
| 6,891,177 B1 * | 5/2005 | Kraft .................... | A61N 5/1042 250/492.1 |
| 9,079,026 B2 * | 7/2015 | Pu .......................... | A61N 5/103 |
| 2012/0004518 A1 | 1/2012 | D'Souza et al. | |
| 2013/0217946 A1 | 8/2013 | Balakin | |
| 2015/0360053 A1 * | 12/2015 | Pu ........................ | A61N 5/1043 600/1 |

FOREIGN PATENT DOCUMENTS

| | | |
|---|---|---|
| EP | 1 683 545 A2 | 7/2006 |
| WO | 2006/012631 A2 | 2/2006 |

OTHER PUBLICATIONS

Extended European Search Report from corresponding Application No. EP 13 18 6787.1, Feb. 3, 2014.

* cited by examiner

*Primary Examiner* — Jack Berman
(74) *Attorney, Agent, or Firm* — Workman Nydegger (57) ABSTRACT

A charged hadron therapy system for delivering charged hadron radiation to a target is provided. The system comprises a target positioning couch for supporting the target being moveable along a translation direction and a beam delivery system comprising a beam scanning means for scanning a hadron pencil beam over said target in a first scanning direction and a second scanning direction being substantially parallel with the translation direction. The beam scanning means is limited for providing a maximum scanning amplitude AY in the second scanning direction. The system comprises an irradiation controller configured for simultaneously and synchronously performing the moving of the couch and the scanning, so as to deliver charged hadron radiation to a target over a target size being larger in the Y direction than the maximum scanning amplitude AY.

15 Claims, 4 Drawing Sheets

CHARGED HADRON BEAM DELIVERY

FIELD OF THE INVENTION

The invention relates to the field of charged hadron radiation therapy. More specifically it relates to a charged hadron particle beam delivery system and a method for charged hadron particle beam delivery.

BACKGROUND OF THE INVENTION

In hadron therapy, a beam of particles composed of quarks, such as protons or positive ions, e.g. carbon ions, is used to selectively irradiate tissue, for example for the treatment of cancer. Such particles may inflict damage to the tissue cells, e.g. particularly to the DNA in these cells. Because of a reduced ability to repair damaged DNA, cancerous cells are known to be particularly vulnerable to such attack. One of the advantages of particle therapy over conventional external beam radiation therapy, e.g. using high-energetic photon irradiation, is the ability to obtain a good localisation of the released energy. Although bremsstrahlung X-rays may penetrate more deeply into the tissue, the absorbed dose in the tissue exponential decays with increasing depth. For protons and heavier ions, the dose increases while the particle penetrates the tissue and loses energy continuously, such that the dose increases to a depth corresponding to the energy-specific Bragg peak near the end of the particle's range. Beyond the Bragg peak, a steep drop to zero or near zero occurs. Thus, by carefully planning the treatment, less energy may be deposited into healthy tissue surrounding the target tissue.

In a known hadron therapy system, the radiation beam may be generated by a charged particle accelerator, such as a cyclotron, synchrocyclotron or synchrotron. The energy of the particle beam, which determines the depth of penetration, e.g. the Bragg peak depth, may be adjusted to the desired range by an energy degrader and selector system. A beam guidance system may further direct the particle beam to a therapy room, in which a patient may be positioned on a therapy couch. A beam delivery system may then deliver the beam to the patient in accordance with a treatment plan. Such beam delivery system may be a fixed beam delivery system for delivering the beam to the patient from a fixed irradiation direction, or may be a rotatable beam delivery system capable of delivering the beam to the patient from a plurality of irradiation directions.

Prior to irradiation, the patient position may be accurately determined and adjusted in order to align the target tissue with the particle beam in accordance with a treatment plan. In order to deliver a spatial dose distribution in the patient which conforms well to a treatment plan defining the target distribution of dose, it is known in the art to use spot or pencil beam scanning In spot or pencil beam scanning systems, the charged particle beam is deflected in a raster scanning pattern, e.g. similar to the manner in which a television image is constructed in a cathode ray tube television. Thus, a pixelated or continuous approximation to the dose delivery plan may be painted in the target volume by modulating the beam intensity or the scanning speed as function of the scanning position. Furthermore, by varying the beam energy, a depth dimension may be added to the dose delivery by iterating the raster scanning process over a plurality of layers defined by different beam energies.

However, the electromagnets in a pencil beam scanning system may be large, heavy and costly. Furthermore, a rotatable beam delivery system may comprise a gantry for selecting a treatment angle with respect to the patient, e.g. for rotating the direction of propagation of the treatment beam around a longitudinal axis of the patient. Since at least part of the pencil beam scanning system may be implemented on such rotatable gantry, weight and size of the pencil beam scanning system components may further increase the cost and size of the overall system, e.g. the gantry.

Therefore, a need exists for reducing the size and weight of pencil beam scanning systems in charged hadron radiation therapy. Unfortunately, reducing the size and weight may also imply a smaller treatment field size, e.g. which is too small for treating targets having a diameter larger than, for example, 5 cm.

SUMMARY OF THE INVENTION

It is an object of embodiments of the present invention to provide good means and methods for charged hadron radiation therapy.

It is an advantage of embodiments of the present invention that the a cost-efficient, compact and light-weight irradiation beam delivery system can be used for irradiating the target, e.g. a patient, over a two-dimensional field by pencil beam scanning.

It is an advantage of embodiments of the present invention that good conformance of a three dimensional dose distribution according to an irradiation plan can be deposited in a target.

It is an advantage of embodiments of the present invention that by performing a scanning in the Y direction, and not only in the X direction, a significant gain in time can be obtained.

It is an advantage of embodiments of the present invention that a cheap and simple system for irradiation is provided, e.g. which comprises a beam deflection means that implements only a first scanning direction, or a beam deflection means that implements only a limited deflection range in a second scanning direction in addition to the first scanning direction.

It is an advantage of embodiments of the present invention that a low weight and small volume of an irradiation beam delivery system can be obtained, facilitating construction and maintenance of e.g. mechanical support and actuation structures, such as e.g. a gantry cage.

It is an advantage of embodiments of the present invention that combined particle beam irradiation and imaging can be performed.

The above objective is accomplished by a method and device according to the present invention.

The present invention relates to a charged hadron therapy system for delivering charged hadron radiation to a target, the system comprising a target positioning couch for supporting said target, the target positioning couch being configured for moving along a translation direction Y', a beam delivery system comprising a beam scanning means for scanning a hadron pencil beam over said target in an first scanning direction X and a second scanning direction Y, the second scanning direction being substantially parallel with the translation direction Y' wherein the beam scanning means is limited for providing a maximum scanning amplitude AY in the second scanning direction Y, and an irradiation controller configured for simultaneously moving the couch along said translation direction (Y') and scanning the hadron pencil beam in X and Y in a synchronized manner, so as to deliver charged hadron radiation to a target over a target size being larger in the Y direction than the maximum scanning amplitude AY. It is an advantage of embodiments of the present invention that by using translation of the target, more efficient irradiation can be obtained resulting in shorter overall irradiation sessions. It is an advantage of embodiments of the present invention that a large scanning field can be obtained, although the available space for irradiation is limited, due to the movement of the couch.

The system furthermore may comprise an irradiation sequencer for determining a sequence of irradiation of different portions of the target to be irradiated, wherein the irradiation sequencer takes into account movement of the couch for determining the sequence. It is an advantage of embodiments of the present invention that although shorter overall irradiation sessions can be obtained by using a scanning technique, still all necessary portions of the target are accurately irradiated.

The system may comprise components downstream the beam scanning means limiting the lateral transmission of the beam of the charged hadron particle beam in the second scanning direction Y to a limitation length, and wherein the scanning amplitude AY is limited to less than the limitation length. It is an advantage of embodiments of the present invention that, although irradiation user time efficiency is increased, the volume of the target that is to be irradiated still can be accurately and fully irradiated, because by using target translation according to a predetermined radiation order of points in the target and/or by translating the irradiation beam.

The irradiation sequencer may be programmed for determining a sequence for scanning spot positions in the target according to a patient treatment plan, the spot positions being part of different energy layers of the patient treatment plan, wherein the sequence defines sub-volumes of the target to be irradiated subsequently taking into account a movement of the couch.

The sub-volumes may be rhomboid shaped sub-volumes or rectangular-shaped sub-volumes. The rhomboid shaped sub-volumes may be parallelepipeds. One of the angles of the parallelepiped may be determined as function of the translation speed of the target. It is an advantage of embodiments of the present invention that, although the use of subvolumes with a shape different from a rectangular-cuboid implies a change in the irradiation order of different points of the target compared to conventional scanning, the use of these shaped subvolumes allows irradiating during movement of the target resulting in shorter irradiation sessions, without parts of the target not being irradiated properly.

The beam scanning means for scanning a hadron pencil beam over said target may be programmed for providing a translation of the charged hadron particle beam synchronously with the translation of the target on the couch during predetermined time periods. The translation speed of the charged hadron particle beam can be the same as the translation speed of the target. The translation speed may be a substantially constant speed. It is an advantage of embodiments of the present invention that no significant accelerations are imposed on the target during the irradiation session. The translation of the target may be substantially rectilinear, except for compensations of movement of the target with respect to the couch.

The beam delivery system furthermore may comprise a gantry being adapted for rotating the pencil beam around the target.

The therapy system may furthermore comprise an imaging means for determining a two-dimensional or three-dimensional image of at least a portion of the target. It is an advantage of embodiments of the present invention that an imaging means is provided that allows checking or cross-checking accurate positioning the target for irradiating it, thus resulting in less damage of parts of the target that should not be irradiated.

The imaging means may comprise a magnetic resonance imaging system, the magnetic resonance imaging system comprising a magnet for generating a magnetic field for aligning the magnetic moment of atomic nuclei in the target, and in which the beam delivery means is arranged for directing the charged hadron pencil beam towards the target through a gap between a first portion and a second portion of the magnet, the gap determining the maximum area of transmission for the pencil beam.

The maximum area of transmission for the pencil beam typically may be the maximum irradiation area for a target that can be momentaneous irradiated using scanning of the pencil beam. The magnetic resonance imaging system may be configured such that the magnetic field is substantially parallel with the Y' axes of the couche, i.e. the direction of translation of the couch.

The present invention also relates to a method for delivering charged hadron radiation to a target, the method comprising moving a couch with a target in a translation direction (Y'), scanning a hadron pencil beam over said target in an first scanning direction (X) and a second scanning direction (Y), the second scanning direction being substantially parallel with the translation direction Y', wherein the scanning in the second scanning direction (Y) is limited to a maximum scanning amplitude AY, and wherein said moving of the couch and said scanning are performed simultaneously in a synchronized manner, so as to deliver charged hadron radiation to a target over a target size being larger in the Y direction than the maximum scanning amplitude AY. The method may comprise sequentially setting the energy of the charged hadron particle beam to each beam energy setting of a sequence of beam energy settings corresponding with different irradiation depths in the target and/or with different positions in the target. The method thus may comprise scanning the charged hadron particle beam over the target in a raster scan pattern in the plane defined by the first scanning direction and the second scanning direction. The method may comprise modulating the beam current of the charged hadron particle beam while translating the target and scanning the charged hadron particle beam over the target, said modulating the beam current taking a predetermined patient treatment plan into account.

The method may comprise translating the charged hadron particle beam synchronously with the translating of the target during predetermined time periods during irradiation of the target.

The method may comprise scanning the beam according to a predetermined sequence for scanning spot positions in the target according to a patient treatment plan, the spot positions being part of different energy layers of the patient treatment plan, wherein the sequence defines sub-volumes of the target to be irradiated subsequently taking into account a movement of the couch.

The sub-volumes are rhomboid shaped sub-volumes or not rectangular-cuboid shaped.

The method may comprise obtaining a two-dimensional or three-dimensional image of at least a portion of the target for obtaining further information about the target.

Obtaining an image may comprise performing magnetic resonance imaging during a charged hadron irradiation session of the target.

A controller for controlling a charged hadron therapy system, the controller being programmed for controlling translating of a target on a couch along a translation direction (Y') and for controlling scanning a hadron pencil beam over said target in an first scanning direction (X) and a second scanning direction (Y) substantially parallel with the translation direction (Y'), wherein the controller is adapted for controlling scanning of the hadron pencil beam in the second scanning direction (Y) with a maximum scanning amplitude AY, and the controller is adapted for simultaneously moving the couch along said translation direction (Y') and scanning the hadron pencil beam in X and Y in a synchronized manner, so as to deliver charged hadron radiation to a target over a target size being larger in the Y direction than the maximum scanning amplitude AY.

The controller may be programmed for controlling the beam delivery system for performing a method as described above.

The present invention also relates to a computer program product and a data carrier comprising a set of instructions for, when executed on a computer, performing a method for delivering charged hadron radiation as described above.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Figure 1:
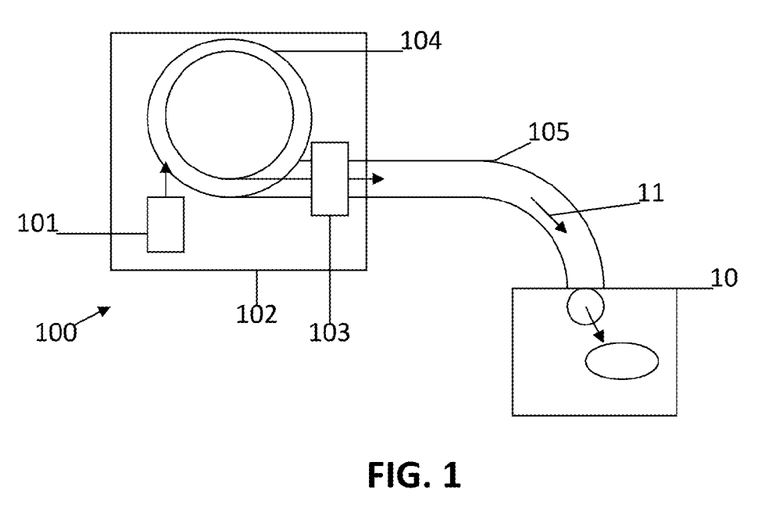
FIG. 1 illustrates a configuration of a charged hadron radiation therapy system according to embodiments of the present invention.

In FIG. 1, a configuration of a charged hadron radiation therapy system 100 according to embodiments of the present invention is schematically shown. Such system may comprise a charged hadron radiation source 102, a beam transport line 105 and a beam delivery system 10. The beam transport line 105 receives a particle beam 11 generated by the charged hadron radiation source 102 and guides this particle beam to the beam delivery system 10. The beam transport line 105 may for example comprise at least one vacuum duct along which the particle beam is guided, and a plurality of magnets, e.g. dipole and/or quadrupole electromagnets, for changing direction of the particle beam and/or adjusting the focusing of the beam. Such systems may also comprise a plurality of beam delivery systems 10, in which the beam transport line 105 is adapted for distributing the particle beam over the plurality of beam delivery systems 10, e.g. by splitting the beam over the plurality of beam delivery systems, and/or by selectively directing the beam to one of the plurality of beam delivery systems. The charged hadron radiation source 102 and the beam delivery system 10 may be arranged in separate shielded rooms, taking into account radiation safety considerations.

The charged hadron radiation source 102 may comprise an injector and an accelerator, in which the injector 101 generates charged hadron particles, such as protons or positive ions, e.g. carbon ions, and the accelerator 104 accelerates the charged hadron particles to provide a high energy charged hadron particle beam, e.g. a proton beam comprising protons which may for example be accelerated to a peak energy in the range of 60 MeV to 350 MeV. The accelerator may for example comprise a cyclotron, synchrotron of synchrocyclotron. The charged hadron radiation source 102 may also comprise energy selection means 103, e.g. a controller for adjusting the energy of the particle beam accelerated by the accelerator. The energy selection means 103 may comprise an energy degrader for degrading the output beam of the accelerator to a selected energy range, for example using absorber blocks, magnetic energy selection magnets and/or collimators. The beam delivery system 10 may for example comprise or be arranged in a treatment room.

Figure 2:
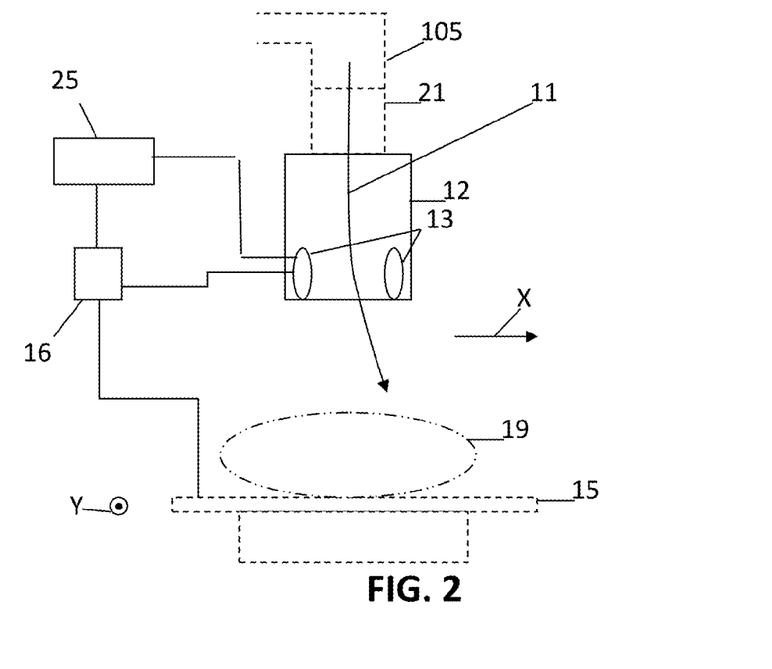
FIG. 2 shows a beam delivery system according to embodiments of the present invention.

In a first aspect, the present invention relates to a charged hadron therapy system for delivering charged hadron radiation to a target, a part thereof being shown in FIG. 2. The therapy system comprises a target positioning couch 15 for supporting the target. According to embodiments of the present invention, the target positioning couch 15 is configured for moving along a translation direction (Y'). The positioning couch 15 may be a powered radiation therapy patient support assembly, e.g. which may comprise an electrically powered adjustable couch intended to support a patient during radiation therapy. Thus, the powered positioning couch 15 may comprise a surface on which the target, e.g. a patient, may be supported during irradiation. The powered positioning couch 15 may comprise at least one actuator, e.g. at least one electric, pneumatic or hydraulic actuator, in order to translate the target along at least one direction Y'. However, in preferred embodiments, the powered positioning couch 15 may also be adapted for translating the target along any direction, e.g. may provide three degrees of freedom for translating the target. The powered positioning couch may also be adapted for rotating the target, e.g. to provide six degrees of freedom for positioning the target with respect to the direction along which the hadron particle beam 11 propagates.

The system also comprises a beam delivery system 10 for delivering the beam to the target. The beam delivery system 10, according to embodiments of the present invention, comprises a beam scanning means. Such a beam scanning means may e.g. be a beam deflection means 13, for example at least one electromagnet, e.g. a scanning electromagnet, for scanning the charged hadron particle beam 11 over the target 19. The beam scanning means may in some embodiments additionally also be adapted for more generally positioning, repositioning or even providing a general movement of the charged hadron particle beam with respect to the target or with respect to components of the therapy system. The beam scanning means may be adapted for scanning in at least one direction, but advantageously is adapted for scanning the charged hadron particle beam 11 in a first scanning direction X and a second scanning direction Y, for example a second scanning direction Y which is substantially orthogonal or which is orthogonal to the first scanning direction X. The second scanning direction Y may be substantially collinear with the translation direction Y' of the translation provided by the couch, for example, may be collinear with the translation direction Y'. The beam scanning means thus may be adapted for scanning the charged hadron particle beam 11 over the target 19 as a pencil beam. The beam scanning means 13 may for example comprise at least one electromagnet receiving a control signal for varying a magnetic field strength according to this control signal. The magnetic field strength may thus be continuously or stepwise varied in order to deflect the charged hadron particle beam over a range of positions defined along the scan directions in a continuous scanning mode or a stepwise scanning mode, for scanning e.g. a raster of points in the target.

In a gantry configuration, the beam deflection means 13 may be implemented in an upstream, a downstream or partly in a downstream and partly in an upstream configuration with respect to the last bending dipole in the gantry.

The therapy system typically also comprises an irradiation controller, also referred to as irradiation control means 16. The control means typically is configured for controlling the scanning of the hadron pencil beam in X and Y, and as will be discussed later to control movement of the couch in a simultaneous and synchronized manner with the scanning, so as to deliver charged hadron radiation to a target over a target size being larger in the Y direction than the maximum scanning amplitude AY.

The control means may be a general purpose programmable controller or computer system with software adapted for the present application or a dedicated digital processing and control hardware system, e.g. comprising an application specific integrated circuit (ASIC). It may be in direct connection with the sequencer 25 or may be part of it.

During the scanning, the control means controls the beam deflection means 13, for example such that a sinusoidal, triangular or ramp profiled variation as function of time of the charged hadron particle beam deflection in at least one direction but advantageously in X and Y direction. The control means may thus supply a suitable wave pattern to the control signal for determining the magnetic field strength of an electromagnet in the beam deflection means. Alternatively, the beam deflection means 13 may be adapted for positioning the beam stepwise according to a raster of points. Optionally, the system also may comprise a beam intensity modulating means (not shown), e.g. a beam current modulating means, and/or a beam energy modulating means (not shown), for controlling a beam current and energy used during therapy.

Alternatively, and more common, beam energy may be selected at or near the beam source, e.g. the cyclotron or synchrotron, as known in the art.

As known in the art, scanning of the beam is not only limited to X and Y scanning, but also includes scanning in the z-direction. By varying the energy of the beam, scanning over a depth dimension, e.g. by varying the penetration depth of the beam, can also be achieved by embodiments according to the present invention. Thus, a preferred or conformal three dimensional dose distribution according to an irradiation plan can be deposited in the target. Advantageously scanning is performed from a deeper layer in the target to a less deep layer in the target.

According to embodiments of the present invention, scanning in the Y direction may be limited, e.g. as components of the system may limit the transmission of the beam and therefore irradiation can only be performed over a limitation length in one direction, e.g. the Y direction.

According to embodiments of the present invention, this limitation in irradiation possibility is overcome by translating the target. The control means 16 may be programmed for controlling the positioning couch 15 such as to translate the target 19 in a translation direction Y', e.g. a constant rectilinear motion. The translation direction may for example be a translation direction not collinear with the first scanning direction X or preferably, a translation direction substantially orthogonal to or orthogonal to the first scanning direction X, for example a translation direction Y' substantially collinear or collinear with the second scanning direction Y. As indicated, the control means is programmed for controlling simultaneously translating the target and for scanning the target with the particle beam. By performing this translation during the scanning, advantageously short irradiation sessions can be obtained. In order to obtain a sufficiently large volume of the target, different portions of the target are irradiated subsequently. For example, when the system has a limitation length for transmission of the beam in one direction, e.g. due to blocking components, the target typically is translated in this direction, thus subsequently bringing portions of the target in the field of view of the beam. These portions are then irradiated by scanning them in one or more sub-volume scans. In this way, only a limited range of deflection is required in the second scanning direction, as a larger target volume may be scanned over by the beam due to the advantageous synchronous translation of the target. For example, the range of deflection in the second scanning direction may be provided by a dipole magnet which may only provide a small range of deflection, e.g. deflecting the beam maximally 10 cm, or less, for example 5 cm, or even less, for example 3 cm, in a beam entry plane defined on the target. The scanning range may be equal to or less than the limitation length in the scanning direction.

In particular embodiments, the target may be positioned in a reference position, from which an irradiation procedure is initiated. During such procedure, the control means may maintain a movement of the target, e.g. a constant rectilinear motion of the target, e.g. may maintain a speed in a range 1 mm to 5 mm per second along the Y axis, while scanning the area for measurement in X and Y direction. The speed may even be smaller, e.g. lower than 1 mm/s, which may for example be beneficial for large tumors, or may be larger, e.g. up to or exceeding 1 cm/s, which may for example be beneficial for small tumours (in combination with very fast scanning). The speed may be determined as function of patient comfort, as function of tumour characteristics, as function of patient treatment characteristics and performances, or as function of a combination thereof.

In one embodiment, the control means may be programmed for compensating the irradiation for target movement by selecting a specific order wherein different points of the target are irradiated. The system therefore may comprise an irradiation sequencer 25 for determining a sequence for determining a sequence for scanning spot positions in the target according to a patient treatment plan. The spot positions may be part of different energy layers of the patient treatment plan. The sequencer may determine a sequence defining sub-volumes of the target to be irradiated subsequently taking into account a movement of the couch. Taking into account a movement of the couch may comprise taking into account the speed of the couch in order to guarantee that the different sub-volumes overall cover the target volume to be irradiated. It may comprise guaranteeing that the different sub-volumes are adjacent. Taking into account a movement also may comprise taking into account the movement speed for controlling the timing of the irradiation in the sequence of irradiated positions. In particular embodiments, as will be illustrated further, the sub-volumes that typically may be scanned, e.g. sub-volumes being not positioned at a side of the target volume to be scanned, can be rhomboid shaped sub-volumes.

The irradiation sequencer 25 may be part of the irradiation controller 16, or the irradiation sequencer 25 may be part of an external treatment planning system (TPS).

In another embodiment, the control means may be programmed for compensating the irradiation for the target movement, so that accurate irradiation of the volume is obtained, by controlling the beam scanning system such that the beam is moved synchronously with the moving target during scanning of a first subvolume of the target and for repositioning the irradiation beam thereafter en scanning a further subvolume while again moving the irradiation beam synchronously with the moving target. This process may be repeated until all subvolumes are scanned. In other words, the control means may be programmed for controlling the positioning of the charged hadron particle beam 11 as function of the translation of the target. Again a sequencer may be used for determining the proper sequence for irradiating different spots of the target.

Figure 3:
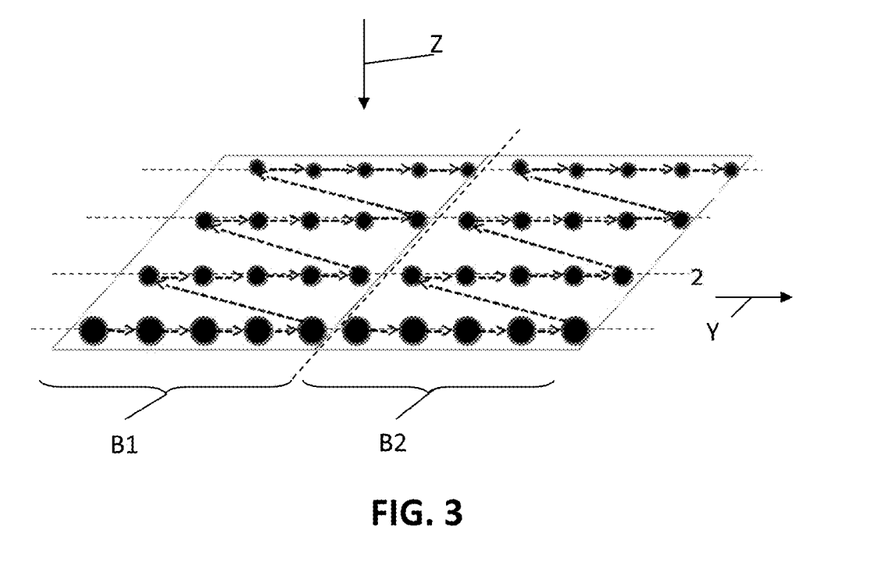
FIG. 3 illustrates an exemplary irradiation sequence relative to the target as can be used in a first embodiment according to the present invention.

FIG. 3 illustrates a first exemplary irradiation sequence executed by a sequencer 25 as controlled by a controller according to the present invention. For example, the sequence may comprise a plurality of batches B1, B2, ..., in which beam energy is varied stepwise such as to iterate over a plurality of dose deposition depth layers along a depth dimension Z in the target, for example in each batch iterating from a maximum predetermined depth to a minimum predetermined depth in a predetermined number of steps. In each depth layer step, the deflection means may be controlled to scan over the second scanning direction, being collinear with the translation direction Y. For example, a plurality of points along the Y direction may be visited by the beam for each depth layer. Due to the translation of the target, a next depth layer will start in a point in the target which is offset relative to the starting point of the previous depth layer, the offset step being determined by the translation and scanning speed. When the plurality of depth steps has been executed for one batch B1, a next batch B2 may be timed to start when the first point in the first depth layer of the next batch B2 aligns, due to the continuous rectilinear motion of the target along the Y axis, with the next point to be irradiated according to a treatment plan, e.g. by selecting an appropriate translation speed for the procedure or by including a short inter-batch time delay. One way to obtain this sequence is by inducing an additional beam translation in line with the movement of the couch, so that during the scanning of the batch, the translation of the target is fully compensated for by an additional translation of the irradiation beam. The limitation induced by the limitation length for transmission of the beam can be overcome by repositioning the beam, in between scanning of different batches. As will be clear for the irradiation scheme shown in FIG. 3, for each point visited, a sweep over the first scanning direction X may also be executed in a shorter time frame as will be apparent to the person skilled in the art, e.g. the Y scanning may be executed at 3 Hz, while the X scanning is executed at a higher frequency, e.g. 30 Hz.

Figure 4:
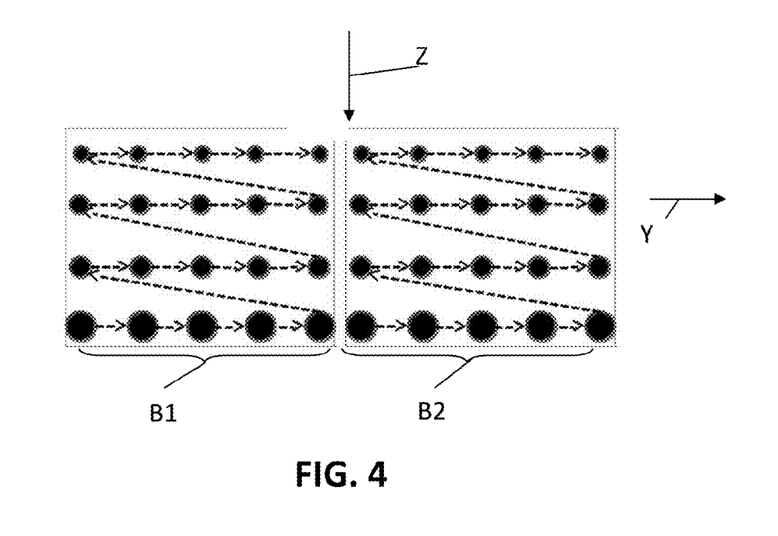
FIG. 4 illustrates an exemplary irradiation sequence relative to the target as can be used in a second embodiment of the present invention.

FIG. 4 illustrates an alternative irradiation sequence. This sequence is similar to the previous described example, e.g. the sequence also comprises a plurality of batches in which beam energy is varied stepwise such as to iterate over a plurality of dose deposition depth layers along the depth dimension Z, but a different subvolume of the target is scanned per batch. In each depth layer step, the deflection means is thus also controlled such as to scan over the second scanning direction, being collinear with the translation direction Y, however, the full limitation length of achievable deflection is not used for each depth layer. Instead, a deflection range window is used, such that the first point of each depth layer in the batch is aligned despite the movement of the target, e.g. the starting position for each scan over a depth layer is shifted in the translation direction to compensate for the distance traversed by the target due to the rectilinear motion over the time of a single depth layer pass.

Although a plurality of discrete points were illustrated in FIG. 3 and FIG. 4, this does not imply that a discrete, e.g. pulsed irradiation procedure is necessarily used. Even though embodiments of the present invention may comprise a pulsed deposition of doses in a plurality of discrete points dispersed over a three-dimensional volume in the target, e.g. a patient, embodiments may equally comprise a continuous dose deposition program, e.g. by continuously varying the beam intensity in accordance with a current point in the target at which the beam is directed and a predetermined irradiation plan. Thus, scanning methods of the pencil beam may include a raster method of performing scanning continuously with respect to time, and a spot method of performing a step-like scanning with respect to time.

The beam delivery system 10 may further also comprise coupling means for receiving the charged hadron particle beam 11 from a beam transport line 105 in a charged hadron radiation therapy system 100. The received beam 11 may then be directed to the target, e.g. via a beam deflection means.

The system according to embodiments illustrated in FIG. 1 may for example correspond to a fixed beam arrangement in a treatment room. The system according to such embodiments offers the advantage of a cheap and simple system for irradiation, e.g. which comprises a beam deflection means that implements only the first scanning direction, or a beam deflection means that implements only a limited deflection range in a second scanning direction in addition to the first scanning direction.

Figure 5:
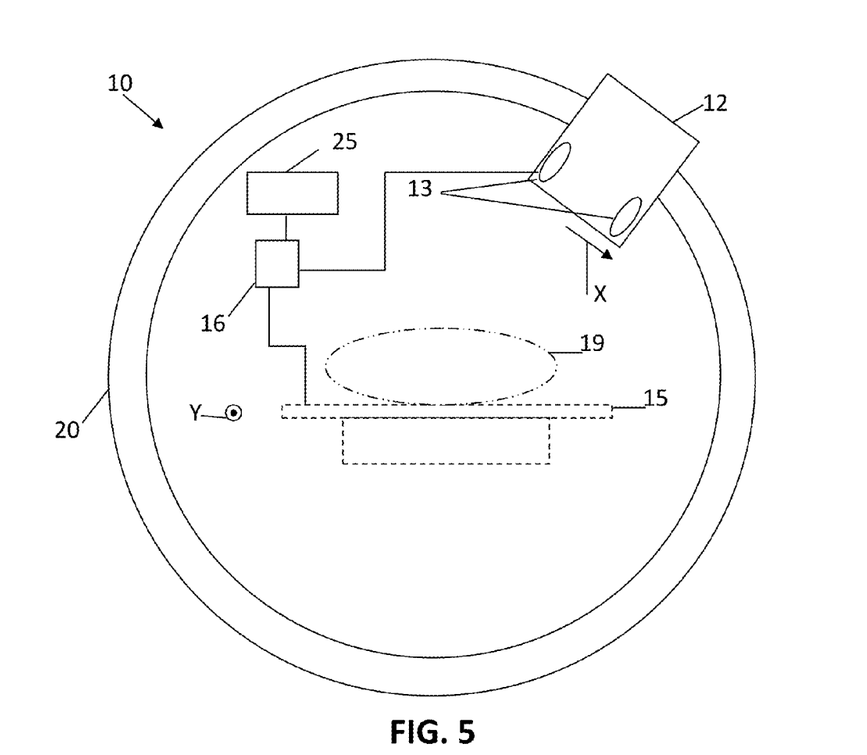
FIG. 5 shows a beam delivery system comprising a rotating gantry arrangement according to embodiments of the present invention.

However, embodiments of the present invention are not limited to fixed beam arrangements. For example, in the system as schematically illustrated in FIG. 5, the beam delivery system 10 also comprises a gantry 20 allowing for beam delivery from different angles to the target. For example, such system may comprise a squirrel cage and beam transport lines as presently known in the art. The beam transport lines may be adapted for supplying the charged hadron particle beam, e.g. from the coupling means 21, to the target from variable angles. The gantry may be adapted for selecting the irradiation angle around an axis substantially collinear with the translation direction Y. Such embodiments according to the present invention have the advantage that the weight and volume of the gantry may be low, thereby facilitating construction and maintenance of the mechanical support and actuation structure.

Figure 6:
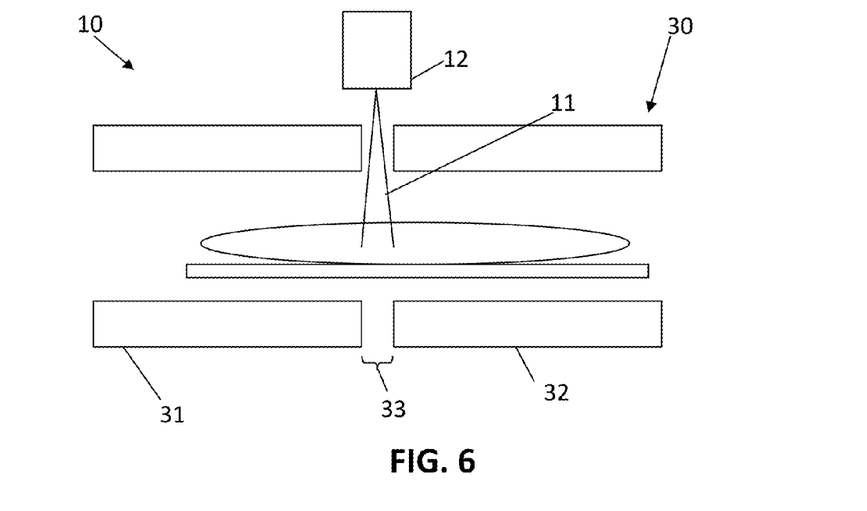
FIG. 6 shows a beam delivery system comprising a magnetic resonance imaging unit according to embodiments of the present invention.

Furthermore, a beam delivery system 10 according embodiments may also comprise an imaging means 30, e.g. a medical imaging system, as shown in FIG. 6, for determining a two-dimensional or three-dimensional image of at least a portion of the target. The imaging means 30 may for example comprise an X-ray imaging device, for example at least one flat panel digital radiography unit or a computed tomography unit, a echography unit, an optical imaging unit, a magnetic resonance unit, or a combination of such imaging means.

The control means 16 may be adapted for receiving an input signal derived from a two-dimensional or three-dimensional image determined by such imaging means 30 and taking such input signal into account while controlling the beam delivery system, e.g. the deflection means 13 and/or the powered positioning couch 19. Such information may for example be used by implementing a gating technique known in the field of radiotherapy. Alternatively or additionally, a relative position of a target structure in the target with respect to the current beam direction and penetration depth may be determined taking into the image in order to dynamically adjust, for example, the beam intensity during irradiation.

It is known that an imaging means 30 in a beam delivery system may pose restrictions on the transmission of the hadron beam or the free spatial angle over which the charged hadron particle beam can be projected. For example, the imaging means 30 may comprise a magnetic resonance imaging system. A magnetic resonance imaging system typically comprises a means for generating a magnetic field, e.g. a large magnet generating a strong magnetic field, e.g. in the range of 0.2 T to 7.0 T, e.g. in the range of 1.0 T to 4.0 T, is used to align the magnetization of atomic nuclei in the target, e.g. particularly hydrogen nuclei.

Although combination of charged particle treatment and magnetic resonance imaging may not be trivial, implementations of such combination systems are known in the art. For example, it is known in the art that a combined magnetic resonance imaging scanner and charged hadron particle irradiation system may comprise a trajectory calculation means for calculating a corrected trajectory of the particle beam using magnetic field data.

In order to enable magnetic resonance imaging of the target volume being irradiated while acquiring the images, it is also known to use an open-bore magnet, in which the gap between the bore segments is used to project the particle beam through. The beam delivery system according to embodiments may thus comprise a magnetic resonance imaging system which comprises an open-bore magnet for generating a magnetic field for aligning the magnetic moment of atomic nuclei in the target. The charged hadron particle beam 11 may be directed toward the target 19 through a gap 33 between a first bore portion 31 and a second bore portion 32 of the open-bore magnet. However, for maintaining sufficient imaging quality, e.g. for achieving the spatial resolution typically required in radiotherapy, the gap width in an open-bore magnet is preferably small, e.g. less than 10 cm, e.g. in the range of 5 cm to 9 cm. Embodiments of the present invention provide means for efficiently irradiating a treatment volume in a target which is substantially larger that the width allowed for by such gap, by translating the target along the Y axis, which may be collinear with the longitudinal axis of the open-bore magnet, while scanning the radiation beam over the range allowed for by the small gap.

In a second aspect, the present invention also relates to a controller for controlling a charged hadron therapy system. The controller is, according to embodiments of the present invention, programmed for controlling translating of a target on a couch along a translation direction (Y') and for controlling scanning a hadron pencil beam over said target in an first scanning direction (X) and a second scanning direction (Y) substantially parallel with the translation direction (Y'). The controller is according to embodiments of the present invention adapted for controlling scanning of the hadron pencil beam in the second scanning direction (Y) with a maximum scanning amplitude AY. The controller is also adapted for simultaneously in a synchronized manner moving the couch along said translation direction (Y') and scanning the hadron pencil beam in X and Y, so as to deliver charged hadron radiation to a target over a target size being larger in the Y direction than the maximum scanning amplitude AY. The controller may be especially suitable for use in a system as described in the first aspect. Further optional features may correspond with those features as described in the first aspect.

In a third aspect, the present invention also relates to a beam delivery method 50 for delivering charged hadron radiation to a target. According to embodiments of the present invention, the method comprises moving a couch with a target in a translation direction (Y') and scanning a hadron pencil beam over said target in an first scanning direction (X) and a second scanning direction (Y), the second scanning direction being substantially parallel with the translation direction Y'. The scanning in the second scanning direction (Y) thereby is limited to a maximum scanning amplitude AY. The moving of the couch and the scanning furthermore are performed simultaneously in a synchronized manner, so as to deliver charged hadron radiation to a target over a target size being larger in the Y direction than the maximum scanning amplitude AY. The method may advantageously be performed using a system as described in the first aspect. Furthermore, the method optionally may comprise additional steps expressing the functionality of device features described for elements of a system according to the first aspect.

Figure 7:
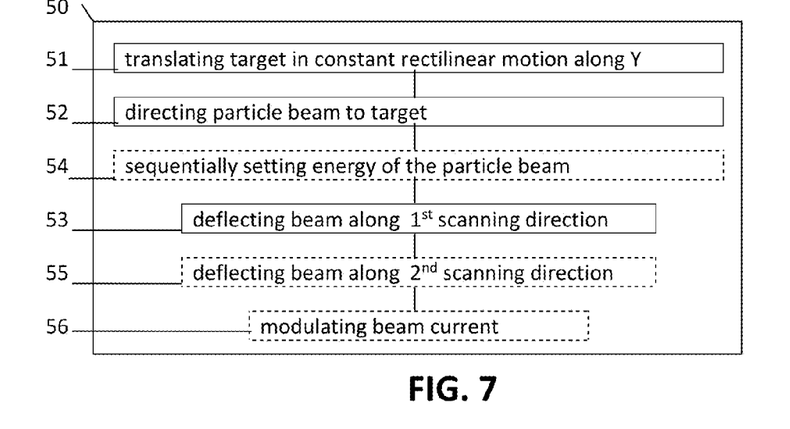
FIG. 7 illustrates a method according to embodiments of the present invention.

An exemplary method according to an embodiment of the present invention is schematically illustrated for illustrative purposes in FIG. 7. Such method comprises the steps of translating 51 a target 19 in a constant rectilinear motion along a translation direction Y and directing 52 a charged hadron particle beam 11 toward the target 19. The method 50 may also comprise generating such charged hadron particle beam 11, and positioning the target 19 into an initial reference position with respect to a beam reference position of the charge hadron particle beam 11 before initiating the translation 51 of the target 19. The method may also comprise obtaining a treatment plan for the target 19, the treatment plan defining a target spatial radiation dose distribution to deposit into the target 19.

The method 50 further comprises deflecting 53 the charged hadron particle beam 11 along a first scanning direction X while translating the target 19 such as to scan the charged hadron particle beam 11 over the target 19. The first scanning direction X may be non-collinear with the direction Y, e.g. may be orthogonal to the translation direction Y, such as to cover a predetermined area defined in a plane defined by the directions X and Y on the target by the simultaneous scanning of the charged hadron particle beam 11 over the target 19 in the scanning direction X and the translation motion of the target in the translation direction Y.

The method 50 may also comprise sequentially setting 54 the energy of the charged hadron particle beam 11 to each beam energy setting of a sequence of beam energy settings, e.g. each setting defining a different depth range of peak radiation dose deposition in the target. The method may thus comprise for each beam energy setting deflecting the charged hadron beam along the first scanning direction X such as to scan the charged hadron particle beam 11 over the target 19.

The method 50 may further comprise deflecting 55 the charged hadron particle beam 11 along a second scanning direction while translating the target 19 such as to scan the charged hadron particle beam 11 over the target 19 in a raster scan pattern in the plane defined by the first scanning direction and the second scanning direction.

The method 50 may also comprise modulating 56 the beam current of the charged hadron particle beam 11 while translating the target 19 and scanning the charged hadron particle beam 11 over the target, the modulating of the beam current being performed by taking a predetermined irradiation plan into account, e.g. to obtain a radiation dose deposition distribution in the target which conforms with the predetermined irradiation plan.

In yet a further aspect, the present invention also relates to a method for controlling a hadron therapy system implemented as a computer implemented invention in a processor and to corresponding processors. One configuration of such a processor may for example include at least one programmable computing component coupled to a memory subsystem that includes at least one form of memory, e.g., RAM, ROM, and so forth. It is to be noted that the computing component or computing components may be a general purpose, or a special purpose computing component, and may be for inclusion in a device, e.g., a chip that has other components that perform other functions. Thus, one or more aspects of the present invention can be implemented in digital electronic circuitry, or in computer hardware, firmware, software, or in combinations of them. For example, each of the method steps may be a computer implemented step. Thus, while a processor as such is prior art, a system that includes the instructions to implement aspects of the method for controlling a hadron therapy system for beam delivery is not prior art.

The present invention thus also includes a computer program product which provides the functionality of any of the methods according to the present invention when executed on a computing device.

In another aspect, the present invention relates to a data carrier for carrying a computer program product for controlling a hadron therapy system. Such a data carrier may comprise a computer program product tangibly embodied thereon and may carry machine-readable code for execution by a programmable processor. The present invention thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non-volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

Figure 8:
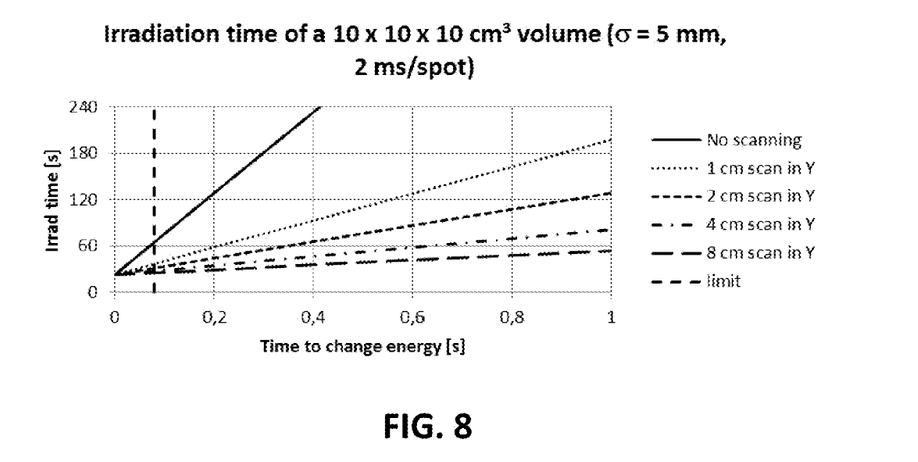
FIG. 8 illustrates simulation results for the irradiation time as function of the time required to change energy for different situations of scanning the patient in the translation direction simultaneously with the translation of the patient, as applied according to embodiments of the present invention.

By way of illustration, embodiments of the present invention not being limited thereto, results of an irradiation time simulation are shown in FIG. 8, whereby the irradiation time as function of the time to change the energy (in seconds) is shown for different situations. The simulation is performed for an exemplary one litre target volume ($10 \times 10 \times 10$ cm$^3$) and assuming that the target is scanned with a beam having a Gaussian profile with a sigma value of 5 mm. The target volume is divided in a number of energy layers and each layer is divided by a number of target spots to be irradiated. It was assumed that, for each spot, it takes about 2 ms to delivery the spot dose. The vertical axis of FIG. 8 indicates the total irradiation time to irradiate the entire target volume, i.e. irradiate all the energy layers and all the spots within each layer. The horizontal axis of FIG. 8 indicates the time to change the energy, i.e. the time to switch from one energy layer to the next layer. The full black line indicates the situation whereby no scanning is performed in the Y direction, as a reference result. Further, the irradiation time is shown for methods whereby scanning in the Y direction during translation of the patient is performed for different maximum scanning amplitudes in the Y direction. Results are shown for a scanning amplitude being 1 cm in the Y direction, 2 cm in the Y direction, 4 cm in the Y direction and 8 cm in the Y direction. It can be seen that simultaneously scanning in the translation direction and translating the patients according to embodiments of the present invention results in a large gain in irradiation time (the irradiation time becoming substantially smaller). It can also be seen that even for small scanning amplitudes this gain in irradiation time is already significant. For example, for an energy switching time of 0.4 seconds and when using a maximum scan amplitude of only 2 cm, the irradiation time is 65 seconds which is to compared with the almost 240 seconds irradiation time if no scanning in Y is applied. The current energy switching time obtained by applicants proton therapy systems is one second. With this one second energy switching and with for example a maximum scanning amplitude in Y of 2 cm, an irradiation time of 128 seconds is obtained for this exemplary target volume. The one second energy switching time could be improved and it is expected that ultimate energy switching times of the order of 100 microseconds might be obtained. Energy switching times of 100 microseconds are at the limit of what is technical feasible. In the graph, the lower limit which can be reached for the time to change the energy also is indicated. If an energy switching time of 100 microseconds could be obtained, it is shown that the irradiation time is reduced from more than 60 seconds down to about 30 seconds when using a device according to the invention and applying a maximum scanning amplitude in Y of 2 cm.

The invention claimed is:

1. A charged hadron therapy system for delivering charged hadron radiation to a target, the system comprising:
    a target positioning couch for supporting said target, the target positioning couch being configured for moving along a translation direction,
    a beam delivery system comprising
    a beam scanning means for scanning a hadron pencil beam over said target in an first scanning direction and a second scanning direction, the second scanning direction being substantially parallel with the translation direction wherein the beam scanning means is limited for providing a maximum scanning amplitude AY in the second scanning direction, and
    an irradiation controller configured for simultaneously moving the couch along said translation direction and scanning the hadron pencil beam in X and Y in a synchronized manner, so as to deliver charged hadron radiation to a target over a target size being larger in the Y direction than the maximum scanning amplitude AY.

2. The charged hadron therapy system according to claim 1, wherein the system furthermore comprises an irradiation sequencer for determining a sequence of irradiation of different portions of the target to be irradiated, wherein the irradiation sequencer takes into account movement of the couch for determining the sequence.

3. The charged hadron therapy system according to claim 1, wherein the system comprises components downstream the beam scanning means limiting the lateral transmission of the beam of the charged hadron particle beam in the second scanning direction Y to a limitation length, and wherein the scanning amplitude AY is limited to less than the limitation length.

4. The charged hadron therapy system according to claim 1, wherein the irradiation sequencer is programmed for determining a sequence for scanning spot positions in the target according to a patient treatment plan, the spot positions being part of different energy layers of the patient treatment plan, wherein the sequence defines sub-volumes of the target to be irradiated subsequently taking into account a movement of the couch.

5. The charged hadron therapy system according to claim 4, wherein said sub-volumes are rhomboid shaped sub-volumes or rectangular-shaped sub-volumes.

6. The charged hadron therapy system according to claim 1, wherein said beam scanning means for scanning a hadron pencil beam over said target is programmed for providing a translation of the charged hadron particle beam synchronously with the translation of the target on the couch during predetermined time periods.

7. The charged hadron therapy system according to claim 1, wherein said beam delivery system furthermore comprises a gantry being adapted for rotating the pencil beam around the target and/or wherein the system further comprises an imaging means for determining a two-dimensional or three-dimensional image of at least a portion of the target.

8. The charged hadron therapy system according to claim 1, wherein the system comprises a magnetic resonance imaging system, the magnetic resonance imaging system comprising a magnet for generating a magnetic field for aligning the magnetic moment of atomic nuclei in the target, and in which the beam delivery means is arranged for directing the charged hadron pencil beam towards the target through a gap between a first portion and a second portion of the magnet, the gap determining the maximum area of transmission for the pencil beam.

9. A method for delivering charged hadron radiation to a target, the method comprising:
    moving a couch with a target in a translation direction,
    scanning a hadron pencil beam over said target in an first scanning direction and a second scanning direction, the second scanning direction being substantially parallel with the translation direction Y',
    wherein the scanning in the second scanning direction is limited to a maximum scanning amplitude AY, and wherein said moving of the couch and said scanning are performed simultaneously in a synchronized manner, so as to deliver charged hadron radiation to a target over a target size being larger in the Y direction than the maximum scanning amplitude AY.

10. The method for delivering charged hadron radiation according to claim 9, wherein the method comprises translating the charged hadron particle beam synchronously with the translating of the target during predetermined time periods during irradiation of the target.

11. The method for delivering charged hadron radiation according to claim 9, wherein the method comprises scanning the beam according to a predetermined sequence for scanning spot positions in the target according to a patient treatment plan, the spot positions being part of different energy layers of the patient treatment plan, wherein the sequence defines sub-volumes of the target to be irradiated subsequently taking into account a movement of the couch.

12. The method for delivering charged hadron radiation according to claim 11, wherein said sub-volumes are rhomboid shaped sub-volumes or not rectangular-cuboid shaped.

13. The method for delivering charged hadron radiation according to claim 9, the method comprising obtaining a two-dimensional or three-dimensional image of at least a portion of the target for obtaining further information about the target and/or the method comprising performing magnetic resonance imaging during a charged hadron irradiation session of the target.

14. The method for delivering charged hadron radiation according to claim 9, the method being implemented as a set of instructions for, when executed on a computer, performing the method.

15. A controller for controlling a charged hadron therapy system,
 the controller being programmed for controlling translating of a target on a couch along a translation direction and for controlling scanning a hadron pencil beam over said target in an first scanning direction and a second scanning direction substantially parallel with the translation direction,
 i) wherein the controller is programmed for controlling scanning of the hadron pencil beam in the second scanning direction with a maximum scanning amplitude AY, and the controller is programmed for controlling simultaneously moving the couch along said translation direction and scanning the hadron pencil beam in X and Y in a synchronized manner, so as to deliver charged hadron radiation to a target over a target size being larger in the Y direction than the maximum scanning amplitude AY.

\* \* \* \* \*